US011058521B2

(12) United States Patent
Tapaltsyan et al.

(10) Patent No.: US 11,058,521 B2
(45) Date of Patent: Jul. 13, 2021

(54) METHOD AND APPARATUS FOR IMPROVING OSSEOINTEGRATION, FUNCTIONAL LOAD, AND OVERALL STRENGTH OF INTRAOSSEOUS IMPLANTS

(71) Applicant: UNIVERSITY OF CENTRAL OKLAHOMA, Edmond, OK (US)

(72) Inventors: Vagan Tapaltsyan, El Cerrito, CA (US); Morshed Khandaker, Edmond, OK (US); Shahram Riahinezhad, Fort Lee, NJ (US); Rami Mohanad Mahdi Alkhaleeli, Edmond, OK (US); Niyaf Nidhal Kadhem Alkadhem, Edmond, OK (US)

(73) Assignee: UNIVERSITY OF CENTRAL OKLAHOMA, Edmond, OK (US)

( * ) Notice: Subject to any disclaimer, the term of this patent is extended or adjusted under 35 U.S.C. 154(b) by 22 days.

(21) Appl. No.: 16/286,005

(22) Filed: Feb. 26, 2019

(65) Prior Publication Data
US 2019/0262105 A1  Aug. 29, 2019
US 2020/0352683 A9  Nov. 12, 2020

Related U.S. Application Data

(63) Continuation-in-part of application No. 16/248,122, filed on Jan. 15, 2019, which is a continuation-in-part
(Continued)

(51) Int. Cl.
*A61C 8/02* (2006.01)
*A61C 8/00* (2006.01)
(Continued)

(52) U.S. Cl.
CPC .......... *A61C 8/0006* (2013.01); *A61C 8/0013* (2013.01); *A61C 8/0016* (2013.01);
(Continued)

(58) Field of Classification Search
CPC ... A61C 8/0006; A61C 8/0013; A61C 8/0015; A61C 8/0016; A61C 13/0018
See application file for complete search history.

(56) References Cited

U.S. PATENT DOCUMENTS

| 692,631 A | 2/1902 | Cooley |
| 1,975,504 A | 10/1934 | Formhals |

(Continued)

FOREIGN PATENT DOCUMENTS

| CN | 1687493 A | 10/2005 |
| CN | 1766181 A | 5/2006 |

(Continued)

OTHER PUBLICATIONS

Translation of WO2015033680. Accessed at Google Patents on Oct. 14, 2020. (Year: 2015).*
(Continued)

*Primary Examiner* — Edward Moran
(74) *Attorney, Agent, or Firm* — Berenato & White, LLC

(57) ABSTRACT

The present invention enables modification of an intraosseous implant device that is not only biologically non-inert, but can stimulate bone and vascular growth; decrease localized inflammation; and fight local infections. The method of the present invention provides a fiber with any of the following modifications: (1) Nanofiber with PDGF, (2) Nanofiber with PDGF+BMP2, and (3) Nanofiber with BMP2 and Ag. Nanofiber can be modified with other growth factors that have been shown to improve bone growth and maturation—BMP and PDGF being the most common. Nanofiber can be applied on the surface of the implant in several ways. First, a spiral micro-notching can be applied on the implant in the same direction as the threads with the nanofibers embedded into the notches. Second, the entire surface of the implant may be coated with a mesh of
(Continued)

nanofibers. Third, it can be a combination of both embedding and notching.

12 Claims, 10 Drawing Sheets

Related U.S. Application Data of application No. 15/791,571, filed on Oct. 24, 2017, now Pat. No. 10,206,780, which is a continuation of application No. 15/467,652, filed on Mar. 23, 2017, now Pat. No. 9,809,906, which is a continuation-in-part of application No. 14/734,147, filed on Jun. 9, 2015, now Pat. No. 10,415,156, said application No. 16/248,122 is a continuation-in-part of application No. 15/976,615, filed on May 10, 2018, now Pat. No. 10,286,103, which is a continuation of application No. 15/674,309, filed on Aug. 10, 2017, now Pat. No. 9,974,883.

(60) Provisional application No. 62/634,993, filed on Feb. 26, 2018, provisional application No. 62/312,041, filed on Mar. 23, 2016, provisional application No. 62/038,506, filed on Aug. 18, 2014, provisional application No. 62/373,786, filed on Aug. 11, 2016.

(51) Int. Cl.
  *A61C 13/00* (2006.01)
  *A61K 6/891* (2020.01)
  *A61K 6/898* (2020.01)

(52) U.S. Cl.
  CPC ........ *A61C 8/0022* (2013.01); *A61C 13/0018* (2013.01); *A61K 6/891* (2020.01); *A61K 6/898* (2020.01)

(56) References Cited

U.S. PATENT DOCUMENTS

| | | | |
|---|---|---|---|
| 2,109,333 A | 2/1938 | Formhals | |
| 2,123,992 A | 7/1938 | Formhals | |
| 2,187,306 A | 1/1940 | Formhals | |
| 2,349,950 A | 5/1944 | Formhals | |
| 4,536,894 A | 8/1985 | Galante et al. | |
| 4,636,219 A | 1/1987 | Pratt et al. | |
| 4,655,769 A | 4/1987 | Zachariades | |
| 5,013,324 A | 5/1991 | Zolman et al. | |
| 5,370,698 A | 12/1994 | Heimke et al. | |
| 5,507,833 A | 4/1996 | Bohn | |
| 5,672,284 A | 9/1997 | Devanathan et al. | |
| 6,106,913 A | 8/2000 | Scardino et al. | |
| 6,312,473 B1 | 11/2001 | Oshida | |
| 6,355,699 B1 | 3/2002 | Vyakarnam et al. | |
| 6,419,491 B1 * | 7/2002 | Ricci ................ A61C 8/0012 433/173 |
| 6,743,273 B2 | 6/2004 | Chung et al. | |
| 6,753,454 B1 | 6/2004 | Smith et al. | |
| 6,821,479 B1 | 11/2004 | Smith et al. | |
| 7,575,707 B2 | 8/2009 | Xia | |
| 7,828,539 B1 | 11/2010 | Beachley et al. | |
| 7,879,093 B2 | 2/2011 | Wei et al. | |
| 8,097,274 B2 | 1/2012 | Coombes et al. | |
| 8,157,554 B2 | 4/2012 | Petras et al. | |
| 8,475,531 B1 | 7/2013 | Maxson et al. | |
| 8,691,542 B2 | 4/2014 | Guilak et al. | |
| 8,728,170 B1 | 5/2014 | Atanasoska et al. | |
| 9,095,524 B2 | 8/2015 | Warnke et al. | |
| 9,180,223 B2 | 11/2015 | Yu et al. | |
| 9,327,448 B2 | 5/2016 | Shah et al. | |
| 9,359,694 B2 | 6/2016 | Khandaker et al. | |
| 9,428,849 B2 | 8/2016 | Haynie et al. | |
| 9,618,501 B2 | 4/2017 | Mohapatra et al. | |
| 9,649,409 B2 | 5/2017 | Guilak et al. | |
| 9,737,632 B2 | 8/2017 | Johnson et al. | |
| 9,809,906 B2 | 11/2017 | Khandaker et al. | |
| 10,206,780 B2 | 2/2019 | Khandaker et al. | |
| 2002/0104606 A1 | 8/2002 | Ohzuru et al. | |
| 2005/0119758 A1* | 6/2005 | Alexander ......... A61F 2/30771 623/23.5 |
| 2005/0137675 A1 | 6/2005 | Dubson et al. | |
| 2005/0142163 A1 | 6/2005 | Hunter et al. | |
| 2005/0224998 A1 | 10/2005 | Andrady et al. | |
| 2005/0276841 A1 | 12/2005 | Davis et al. | |
| 2006/0226580 A1 | 10/2006 | Xia et al. | |
| 2007/0269481 A1 | 11/2007 | Li et al. | |
| 2007/0275458 A1 | 11/2007 | Gouma | |
| 2008/0112998 A1 | 5/2008 | Wang | |
| 2008/0170982 A1 | 7/2008 | Zhang et al. | |
| 2008/0290554 A1 | 11/2008 | Wu et al. | |
| 2009/0108503 A1 | 4/2009 | Scott-Carnell et al. | |
| 2009/0118813 A1 | 5/2009 | Scheuermann et al. | |
| 2009/0196901 A1 | 8/2009 | Guilak et al. | |
| 2009/0226600 A1 | 9/2009 | Dang et al. | |
| 2009/0294733 A1 | 12/2009 | Branham et al. | |
| 2009/0324680 A1 | 12/2009 | Reneker et al. | |
| 2009/0324950 A1 | 12/2009 | Kim | |
| 2010/0009267 A1 | 1/2010 | Chase et al. | |
| 2010/0028387 A1 | 2/2010 | Balasundaram et al. | |
| 2010/0028999 A1 | 2/2010 | Nain | |
| 2010/0113857 A1 | 5/2010 | Ramakrishna et al. | |
| 2010/0119578 A1 | 5/2010 | To et al. | |
| 2010/0168771 A1 | 7/2010 | Guldberg et al. | |
| 2010/0197027 A1 | 8/2010 | Zhang et al. | |
| 2010/0310623 A1 | 12/2010 | Laurencin et al. | |
| 2010/0327494 A1 | 12/2010 | Jabbari | |
| 2010/0331980 A1 | 12/2010 | Lee et al. | |
| 2011/0066242 A1 | 3/2011 | Lu et al. | |
| 2013/0030452 A1 | 1/2013 | Itskovitz-Eldor et al. | |
| 2013/0110138 A1 | 5/2013 | Hurtado et al. | |
| 2013/0115457 A1 | 5/2013 | Haynie et al. | |
| 2013/0273801 A1 | 10/2013 | Young | |
| 2014/0079759 A1 | 3/2014 | Patel et al. | |
| 2014/0205971 A1 | 7/2014 | Wang | |
| 2014/0271786 A1 | 9/2014 | Bagga et al. | |
| 2014/0271795 A1 | 9/2014 | Phaneuf et al. | |
| 2015/0165092 A1 | 6/2015 | Kaplan et al. | |
| 2015/0273110 A1 | 10/2015 | McClellan et al. | |
| 2015/0283298 A1 | 10/2015 | Kaplan et al. | |
| 2015/0290354 A1 | 10/2015 | Loboa et al. | |
| 2016/0015483 A1* | 1/2016 | Kumar ................ A61C 8/0075 606/301 |
| 2016/0047063 A1 | 2/2016 | Khandaker et al. | |
| 2016/0047064 A1 | 2/2016 | Khandaker et al. | |
| 2016/0106886 A1 | 4/2016 | Dvir et al. | |
| 2016/0228611 A1 | 8/2016 | Castro et al. | |
| 2016/0250393 A1 | 9/2016 | Jeong et al. | |
| 2016/0374820 A1 | 12/2016 | Khandaker et al. | |
| 2017/0072089 A1 | 3/2017 | Nseir Manassa et al. | |
| 2017/0100912 A1 | 4/2017 | Tricoli et al. | |
| 2017/0130194 A1 | 5/2017 | Lee et al. | |
| 2017/0143874 A1 | 5/2017 | Vickers | |
| 2017/0167064 A1 | 6/2017 | Taylor et al. | |
| 2018/0057963 A1 | 3/2018 | Khandaker et al. | |
| 2018/0161185 A1 | 6/2018 | Kresslein et al. | |
| 2018/0193209 A1 | 7/2018 | Rajamani et al. | |
| 2018/0221146 A1 | 8/2018 | Jana et al. | |
| 2018/0221537 A1 | 8/2018 | Johnson et al. | |
| 2018/0230626 A1 | 8/2018 | Knothe Tate | |

FOREIGN PATENT DOCUMENTS

| | | |
|---|---|---|
| CN | 1776033 A | 5/2006 |
| CN | 103893828 A | 7/2014 |
| CN | 104906637 A | 9/2015 |
| EP | 2045375 A1 | 4/2009 |
| WO | WO2004074559 A1 | 9/2004 |
| WO | WO2005073442 A1 | 8/2005 |
| WO | WO2005123995 A1 | 12/2005 |
| WO | WO2006052039 A1 | 5/2006 |

(56) References Cited

FOREIGN PATENT DOCUMENTS

| WO | WO2006135147 A1 | 12/2006 |
| WO | WO2009101472 A2 | 8/2009 |
| WO | WO2015033680 | * 3/2015 |

OTHER PUBLICATIONS

Hirota et al. "Bone Adaptation of Fibronectin Immobilized Titanium Implants Using a Tresyl Chloride-Activated Method". Journal of Hard Tissue Biology. 24-4, pp. 341-346; 2015 (Year: 2015).*
Ali et al., "Electrospinning of Continuous Nanofiber Bundles and Twisted Nanofiber Yarns", Nanofibers—Production, Properties and Functional Applications, 2011, pp. 153-174.
Bashar Haseeb, "Controlled deposition and alignment of electrospun PMMA-g-PDMS nanofibers by novel electrospinning setups", Master of Science Thesis, KTH Chemical Science and Engineering, Stockholm, Sweden 2011, 164 pages.
KdScientific, "Inflowmation Chronicles Highlights of Interesting Scientific Applications", Inflowmation Chronicles, Issue 1001, Spring 2009, 2 pages.
Li et al., "Electrospinning of Nanofibers: Reinventing the Wheel? **", Advanced Materials, 2004, vol. 16, No. 14, pp. 1151-1170.
Monika Rajput, "Optimization of Electrospinning Parameters to Fabricate Aligned Nanofibers for Neural Tissue Engineering", A Thesis Submitted in Partial Fulfillment of the Requirement for the Degree of Master of Technology in Biotechnology & Medical Engineering, Department of Biotechnology and Medical Engineering, National Institute of Technology, Rourkela, Orissa, India, 2012, 74 pages.
Neves et al., "Patterning of polymer nanofiber meshes by electrospinning for biomedical applications", International Journal of Nanomedicine, 2007, 2(3), pp. 433-448.
Peterson, "Hybrid Nanomanufacturing Process for High-Rate Polymer Nanofiber Production", University of Nebraska—Lincoln, DigitalCommons@University of Nebraska—Lincoln, Engineering Mechanics Dissertations & Theses, 2010, 159 pages.
Tan et al., "Tensile testing of a single ultrafine polymeric fiber", Biomaterials 26, 2005, pp. 1453-1456.
Theron et al., "Electrostatic field-assisted alignment of electrospun nanofibres", Nanotechnology, 12, 2001, pp. 384-390.
Yarin et al., "Branching in electrospinning of nanofibers", Journal of Applied Physics 98, pp. 064501, 2005, pp. 1-12.
Carnell, Lisa A., et al., "Aligned Mats from Electrospun Singer Fibers", Macromolecules, vol. 41, No. 14, Jun. 26, 2008, pp. 5345-5349.
Jianfeng Zhange, et al., "Preparation of biaxial orientation mats from single fibers," Advances in Polymer Technol. Wiley and Sons, Hoboken NJ, vol. 21, Jan. 1, 2018, pp. 606-608.
Partial EP search report for corresponding EP15833663 dated Apr. 12, 2018.
Yee, W.A., et al., "Stress-induced structural changes in electrospun polyvinylidene difluoride nanofibers collected using a modified rotating disk," Polymer, Elsevier Science Publishers, VG, GB vol. 49, No. 19, Sep. 2008, pp. 4196-4203.
Zussman E., et al., "Assembly of electronspun nanofibers into crossbars," Nanotechnology, 2002, IEEE-NANO 2002, Proceedings of the 2002 2nd IEEE Conference on Aug. 26-28, 2002, Piscataway, NJ, Aug. 26, 2002, pp. 283-286.
Khandaker, M.; Vaughan, M.; Coles, A.; Jamadagni, H.; Wolf, R.; Williams, W. Application of polycaprolactone nanofibers and mgo nanoparticles for a cemented implant surgery. In Proceedings of the 2017 Orthopaedic Research Society (ORS) Annual Meeting, San Diego, CA, USA, Mar. 19-22, 2017.
Po-Yee Lui, P.; Zhang, P.; Chan, K.-M.; Qin, L. Biology and augmentation of tendon-bone insertion repair. J. Orthop. Res. Surg. Res. 2010, 5.
Apedo, K.L.; Munzer, C.; He, H.; Montgomery, P.; Serres, N.; Fond, C.; Feugeas, F. Cement paste surface roughness analysis using coherence scanning interferometry and confocal microscopy. Mater. Charact. 2015, 100, 108-119.
Sultanova, Z.; Kaleli, G.; Kabay, G.; Mutlu, M. Controlled release of a hydrophilic drug from coaxially electrospun polycaprolactone nanofibers. Int. J. Pharm. 2016, 505, 133-138.
Wang, H.B.; Mullins, M.E.; Gregg, J.M.; Hurtado, A.; Oudega, M.; Trombley, M.T.; Gilbert, R.J. Creation of highly aligned electrospun poly-l-lactic acid fibers for nerve regeneration applications. J. Neural Eng. 2009, 6, 016001.
Deravi, L.F.; Sinatra, N.R.; Chantre, C.O.; Nesmith, A.P.; Yuan, H.; Deravi, S.K.; Goss, J.A.; MacQueen, L.A.; Badrossamy, M.R.; Gonzalez, G.M.; et al. Design and fabrication of fibrous nanomaterials using pull spinning. Macromol. Mater. Eng. 2017, 302.
Khandaker, M.; Vaughan, M.; Morris, T.; White, J.; Meng, Z. Effect of additives particles on mechanical, thermal and cell functions properties of poly (methyl methacrylate) cement. Int. J. Nanomed. 2014, 9, 2699-2712.
Graham, J.; Ries, M.; Pruitt, L. Effect of bone porosity on the mechanical integrity of the bone-cement interface. J. Bone Jt. Surg. Am. vol. 2003, 85A, 1901-1908.
Kwon, I.K.; Kidoaki, S.; Matsuda, T. Electrospun nano- to microfiber fabrics made of biodegradable copolyesters: Structural characteristics, mechanical properties and cell adhesion potential. Biomaterials 2005, 26, 3929-3939.
Kumbar, S.G.; James, R.; Nukavarapu, S.P.; Laurencin, C.T. Electrospun nanofiber scaffolds: Engineering soft tissues. Biomed. Mater. 2008, 3.
Kim, G.H. Electrospun pcl nanofibers with anisotropic mechanical properties as a biomedical scaffold. Biomed. Mater. 2008, 3.
Chong, L.H.; Hassan, M.I.; Sultana, N. Electrospun polycaprolactone (pcl) and pcl/nano-hydroxyapatite (pcl/nha)-based nanofibers for bone tissue engineering application. In Proceedings of the 10th Asian Control Conference (ASCC), Kota Kinabalu, Malaysia, 31 MaI Jun. 3, 2015; pp. 1-4.
Moursi, A.M.; Winnard, A.V.; Winnard, P.L.; Lannutti, J.J.; Seghi, R.R. Enhanced osteoblast response to a polymethylmethacrylate-hydroxyapatite composite. Biomaterials 2002, 23, 133-144.
Mahalingam, S.; Edirisinghe, M. Forming of polymer nanofibers by a pressurised gyration process. Macromol. Rapid Commun. 2013, 34, 1134-1139.
Hickey et al., "Adding MgO Nanoparticles to Hydroxyapatite-PLLA Nanocomposites for Improved Bone Tissue Engineering Applications.", Acta Biomaterialia Dec. 2014, https://doi.org/10.1016/j.actbio.2014.12.004.
Saha, S.; Pal, S. Improvement of mechanical properties of acrylic bone cement by fiber reinforcement. J. Biomech. 1984, 17, 467-478.
Kanungo, I.; Fathima, N.N.; Rao, J.R.; Nair, B.U. Influence of pcl on the material properties of collagen based biocomposites and in vitro evaluation of drug release. Mater. Sci. Eng. C Mater. Biol. Appl. 2013, 33, 4651-4659.
Ries, M.D.; Rauscher, L.A.; Hoskins, S.; Lott, D.; Richman, J.A.; Lynch, F. Intramedullary pressure and pulmonary function during total knee arthroplasty. Clin. Orthop. Relat. Res. 1998, 356, 154-160.
Invitrogen. Click-it® Edu Imaging Kits. Available online: https://tools.thermofisher.com/content/sfs/manuals/mp10338.pdf (accessed on Oct. 26, 2017).
Liu et al Surface modification of titanium, titaniaum alloys, and related materials for biomedical applications., Materials Science and Engineering R 47 (2004), 73 pages.
Zupancic, S.; Baumgartner, S.; Lavric, Z.; Petelin, M.; Kristl, J. Local delivery of resveratrol using polycaprolactone nanofibers for treatment of periodontal disease. J. Drug Deliv. Sci.Technol. 2015, 30 Pt B, 408-416.
Wu, X.; Mahalingam, S.; VanOosten, S.K.; Wisdom, C.; Tamerler, C.; Edirisinghe, M. New generation of tunable bioactive shape memory mats integrated with genetically engineered proteins. Macromol. Biosci. 2017, 17.
Moffat, K.L.; Wang, I.N.; Rodeo, S.A.; Lu, H.H. Orthopedic interface tissue engineering for the biological fixation of soft tissue grafts. Clin. Sports Med. 2009, 28, 157-176.
Travan, A.; Marsich, E.; Donati, I.; Foulc, M.-P.; Moritz, N.; Aro, H.T.; Paoletti, S. Polysaccharide-coated thermosets for orthopedic applications: From material characterization to in vivo tests. Biomacromolecules 2012, 13, 1564-1572.

(56) References Cited

OTHER PUBLICATIONS

Lim, J.Y.; Shaughnessy, M.C.; Zhou, Z.; Noh, H.; Vogler, E.A.; Donahue, H.J. Surface energy effects on osteoblast spatial growth and mineralization. Biomaterials 2008, 29, 1776-1784.

Im, B.J.; Lee, S.W.; Oh, N.; Lee, M.H.; Kang, J.H.; Leesungbok, R.; Lee, S.C.; Ahn, S.J.; Park, J.S. Texture direction of combined microgrooves and submicroscale topographies of titanium substrata influence adhesion, proliferation, and differentiation in human primary cells. Arch. Oral Biol. 2012, 57, 898-905.

Ferraz, E.P.; Sa, J.C.; De Oliveira, P.T.; Alves, C., Jr.; Beloti, M.M.; Rosa, A.L. The effect of plasma-nitrided titanium surfaces on osteoblastic cell adhesion, proliferation, and differentiation. J. Biomed. Mater. Res. Part A 2014, 102, 991-998.

Zankovych, S.; Diefenbeck, M.; Bossert, J.; Mückley, T.; Schrader, C.; Schmidt, J.; Schubert, H.; Bischoff, S.; Faucon, M.; Finger, U.; et al. The effect of polyelectrolyte multilayer coated titanium alloy surfaces on implant anchorage in rats. Acta Biomater. 2013, 9, 4926-4934.

Biggs, M.; Dalby, M.; Wilkinson, C.; Gadegaard, N.; Richards, G. The influence of nanoscale biomimetic structures on osteoblast adhesion. Comp. Biochem. Physiol. Part A Mol. Integr. Physiol. 2007, 146, S64.

Wagner, H.D.; Cohn, D. Use of high-performance polyethylene fibres as a reinforcing phase in poly(methylmethacrylate) bone cement. Biomaterials 1989, 10, 139-141.

Wenying Liu, Electrospun Nanofibers for Regenerative Medicine, 2012, Adv Healthc Mater, pp. 1-28.

Xie et al. Silver Nanoparticles and Growth Factors Incorporated Hydroxyapatite Coatings on Metallic Implant Surfaces for Enhancement of Osteoinductivity and Antibacterial Properties, ACS Appl. Mater. Interfaces, 2014, 2 pages.

\* cited by examiner

METHOD AND APPARATUS FOR IMPROVING OSSEOINTEGRATION, FUNCTIONAL LOAD, AND OVERALL STRENGTH OF INTRAOSSEOUS IMPLANTS

CROSS REFERENCES TO RELATED APPLICATIONS

This application is a continuation-in-part of and claims the benefit of priority of U.S. patent application Ser. No. 16/248,122 filed Jan. 15, 2019 by the University of Central Oklahoma (Applicant), entitled "Nanofiber coating to improve biological and mechanical performance of joint prosthesis" the entire disclosure of which is incorporated herein by reference in its entirety for all purposes. This application claims the benefit of U.S. Provisional Patent Application No. 62/634,993 filed on Feb. 26, 2018 in the name of Vagan Tapaltsyan and Morshed Khandaker, which is expressly incorporated herein by reference in its entirety and to which priority is claimed.

STATEMENT AS TO RIGHTS TO INVENTIONS MADE UNDER FEDERALLY SPONSORED RESEARCH OR DEVELOPMENT

This invention was made with government support under Grant Number 5P20GM103447 awarded by the National Institutes of Health. The government has certain rights in the invention.

FIELD OF THE INVENTION

The present invention generally relates to the field of polymer fiber production and biomedical applications thereof. More specifically, the invention relates to improving performance of metallic dental implants by attachment of augmented electrospun fibers exhibiting micron to nano size diameters.

BACKGROUND OF THE INVENTION

Polycaprolecton (PCL) Electrospun Nanofibers (ENF) have numerous biomedical applications. Co-pending application Ser. No. 14/734,147 and U.S. Pat. No. 9,359,694 by the present Applicant discloses a method and apparatus for controlled deposition of branched electrospun fiber on biomedical implants and material, the disclosures of which are incorporated herein by reference in the entirety. Research has shown that micron to nano size fibers may be fused with biomedical implants for improving the mechanical and biological adhesion of titanium implants with the host tissue. Nano size fibers have been found to be excellent carriers of drugs for improving bone growth. If applied as a coating around the implant, improved bone growth may reduce the implant loosening problem. U.S. Pat. Nos. 10,206,780 and 9,809,906 by the present Applicant disclose methods to achieve adhesion of functional nanofiber coatings on a biomedical implant surface to increase the osteoinductive properties, and thereby to improve osseointegration of an implant, the disclosures of which are incorporated herein by reference in the entirety. The method uses PCL ENF fiber applied as a coating material, forming an extracellular matrix on an implant to improve ENF fiber adhesion with an implant surface, enabling use at physiological load bearing conditions. The method supports attachment of ENF fibers to an implant surface for both regular and irregular shape implants and enables drug delivery to promote bone growth.

The loss of teeth is a significant public health issue, increasing the risk of a wide range of conditions such as malnutrition due to lack of proper masticatory function and clinical depression due to the change in facial appearance. Tooth loss is primarily caused by periodontal disease, dental caries, or trauma. The prevalence of all risk factors of tooth loss increases with age and is thus projected to increase with the growth of the aging population across the world. In the United States, the population over 65 years of age is projected to reach 83.7 million by 2050. Though the success rate of dental implant surgery is high, the failure of implants due to poor osseointegration has been reported.

Threaded endosseous devices with a cylindrical or tapered shape are the most widely used type of dental implant. Endosseous dental implants are surgically inserted into the jawbone. Osseointegration refers to bone grown right up to the implant surface without interposed soft tissue layer. Alveolar bone osseointegrates with the implant without development of a periodontal ligament. In cases of decreased primary stability of the implant in bone, micromotions occur at the implant surface that lead to osteoclast-driven resorption of bone around the implant, contributing to further implant loosening and eventual implant failure. Delayed bone healing leads to potential failure of the dental implant. Along with physical pain and suffering, implant loosening due to poor osseointegration and healing leads to economic burdens.

Healing, surgical success, and complete osseointegration are regarded as the most important characteristics of dental (and, to large extent, orthopedic) intraosseous implants. Currently, efforts to improve implant success and osseointegration rates focus on the mechanical aspects of implants, such as the type of alloy, taper, screw thread design, metal finish (acid and laser etching, polishing), etc. All intraosseous devices of the above classes are classified as biologically inert implants, as implant integration occurs through a process of bone remodeling, resulting in total ankylosis. Another approach to improve osseointegration is the direct attachment of osteoinductive nanoscale topographies on endosseous dental implant surfaces. The main concern related to coating nanoscale materials onto an implant surface is the risk of coating detachment and toxicity of related debris. Further, implant length and diameter are important in determining the stability of the implant and the maximum load that can be placed on the implant. Generally, at least 7-9 mm of bone depth is required for implant placement, with implant width varying from 3-7 mm in diameter. These dimensions often act as limiting factors when insufficient bone is present for implant placement. Thus, there is a need for stronger implants with higher functional loads and osseointegration.

SUMMARY OF THE INVENTION

The present invention is directed to increasing success rate of implant surgeries and decreasing integration time independent of the physical properties of implants. The present invention is unique in that it provides a method of incorporating a system of bioaugmentation of metal implants by introducing a PCL ENF carrying a recombinant growth factor, such as BMP2 (Bone Morphogenetic Protein 2) or PDGF (Platelet Derived Growth Factor). These growth factors have been extensively shown to activate neural crest-derived bone stem cells to aid in differentiation, regeneration, and maturation of bone. Moreover, the properties of the fiber allow for binding to an antibiotic agent, such as silver nanoparticles (Ag NP), thus making the implant itself to exhibit antiomicrobial properties, decreasing the risk of implant failure due to infection.

The aforementioned innovations can result in higher stability and retention of intraosseous implants. Thus, while current dental bio-inert implants require 7-9 mm of bone depth, addition of modified PCL ENFs may decrease that requirement due to growth factor-driven improved bone quality and improved osseointegration. Also, current bio-inert implants require 4-6 months for complete osseointegration, while PCL ENF modification may significantly reduce the osseointegration time and speed up recovery. Finally, the present invention may allow for a wider range of acceptable surgical sites for implant placement due to the ENF's ability to stimulate new bone growth.

The present invention enables modification of an intraosseous implant device that is not only biologically non-inert, but can (1) stimulate bone and vascular growth (2) decrease localized inflammation, and (3) fight local infections. The method of the present invention provides a fiber with at least any of the following modifications:

1. Nanofiber with PDGF
2. Nanofiber with PDGF+BMP2
3. Nanofiber with BMP2 and Ag Further, nanofiber can be modified with many growth factors that have been shown to play a role in regulation of physiological bone remodeling to improve bone growth and maturation. These may include, for example, IGFs, TGF-β, FGFs, EGF, and WNTs, as well as BMP and PDGF. Bone development, remodeling, and repair requires attraction of mesenchymal progenitor cells (MPC) and differentiation of MPC into osteoblasts. The effect of rhBMP-2, rxBMP-4, and rhPDGF-bb as chemoattractive proteins for primary human MPC has been shown to be highly significant. Thus, BMP and PDGF are the most commonly ones employed.

Titanium-based implants have been widely used in orthopedics and orthodontic surgeries because of their strong mechanical, chemical and biological properties. We have tested a set of steps (e.g. grooving and oxidizing) by which a nanofiber matrix (NFM), composed of collagen (CG) and poly-ε-caprolactone (PCL) electrospun nanofibers, can be coated on a Ti implant without subsequent detachment. A significantly improved osseointegration of CG-PCL NFM-coated Ti over non-coated Ti not previously known was observed in our experiments. The advantage of functional coating treatment on an implant is that it is simple, indirect, scalable, inexpensive, and supplementary to other surface treatment techniques. Such treatment can be applied on an implant surface without affecting other implant factors, such as mechanical, medication (e.g. drugs, irradiation), and patient (e.g. age, osteopenia) factors. The biological properties of a functional coating can be further improved by adding growth factors, proteins, and other molecules to create a truly osteoinductive platform at the implant/bone interface.

In one major aspect the present invention provides an improved intraosseous implant device capable of decreasing the time periods for osseointegration and preventing post-operative local infections. Titanium (Ti) alloy is most widely used as a dental implant material. We have developed a novel method of coating cylindrical Ti implants with nanofiber mesh by microgrooving. We have also immobilized fibronectin (FN), a glycoprotein of the extracellular matrix, on a Ti alloy (Ti-6Al-4V) by tresyl chloride-activation method. Our studies show that microgrooving on cylindrical Ti implants and subsequent coating of the grooves with collagen-poly-c-caprolactone nanofiber matrix (CG-PCL NFM) significantly improves the biocompatibility, mechanical stability and osseointegration of Ti. A laser pulse can create microgrooves on the surface of regular- and irregular-shaped implants. A literature search has revealed no reported research directed to the controlled fabrication of microgrooves on a complex-shaped implant surface, such as a dental implant (FIG. 1). The effect of coating the laser-induced microgrooves with bone morphogenetic protein-2 (BMP2)- and silver (Ag) nanoparticle (NP)-immobilized PCL NFM on a dental implant has not been reported. Attachment of BMP2 and Ag NP onto Ti dental implant is sought via FN and CG immobilized PCL NFM, respectively. The above mentioned surface treatments on a dental implant may have the potential to improve the implant osseointegration, reducing both healing time, and risk of infection.

In another major aspect the present invention provides methods for attachment of osseointegration-promoting and anti-bacterial biomolecules on a dental implant using laser-induced microgrooves and PCL NFM. Immobilization of BMP2 with PCL NFM (referred as BMP2-PCL) and subsequent coating of a laser-microgrooved titanium implant by BMP2-PCL may lead to greater in vitro and in vivo osteogenic functions in comparison to the non-treated implants due to higher biological compatibility of the BMP2-PCL-coated implant. Immobilization of Ag NP with PCL NFM (referred as Ag-PCL) and subsequent coating of a laser-microgrooved titanium implant by Ag-PCL may lead to lower risk of bacterial development in comparison to the non-treated implants due to higher anti-bacterial resistance of the Ag-PCL-coated implant.

In another major aspect the present invention provides methods for fabrication of the control microgrooves at the interspace between two threads of a dental implant. Fabrication of such grooves can have medical benefits, since grooves on implants induce a higher amount of implant-bone contact area and osteoblast cell function in comparison to implants without grooves. During implantation, the implant body is strongly torqued and drilled into hard bone. The microgrooves protect the functional NFM coating from these applied loads. The NFM coating can serve as a reservoir at the microgrooves on dental implant surfaces for controlled release of bone growth factor and anti-bacterial molecules for reducing infection and promoting osteogenesis. Laser pulse is a method used to produce high precision, high roughness, and uniform microgroove topography on a dental implant along the threaded and non-threaded sections.

In another major aspect the present invention provides methods for attachment of the functional PCL NFM coating on a dental implant of any size or shape. Tresyl chloride, a chemical activation technique, can be used to attach FN on the dental implant surface directly. The bone growth signaling factors and collagen binding domain of FN can be utilized to attach bone growth factors (BMP2) and anti-bacterial molecules (Ag NP) immobilized PCL NFM with Ti. The combined effect of FN immobilization on laser-microgrooved Ti and coating those grooves by PCL NFM provides a novel technique to attach the functional PCL NFM coating on any Ti implant.

In another major aspect the present invention provides methods for a direct immobilization technique using bone growth factors (BMP2) and anti-bacterial molecules (Ag NP) on a human dental implant surface via PCL NFM. A potential opportunity for the advancement of in-vivo tissue-to-implant osseointegration, faster healing times, and reduction of infection of a dental implant are possible from these inventions. Such treatment methods can be applied not only to improve dental implant-to-bone interface, but also to anchor many other orthopedic biomaterials.

Nanofiber can be applied on the surface of an implant in several ways. First, a spiral micro-notching can be applied on the implant in the same direction as the threads, with the nanofibers embedded into the notches. Second, the entire surface of the implant may be coated with a mesh of nanofibers. Third, it can be a combination of both embedding and notching.

DETAILED DESCRIPTION OF PREFERRED EMBODIMENTS OF THE INVENTION

Our research demonstrates: (1) immobilization of ECM proteins (CG and FN) and bone growth factors (BMP2) with PCL NFM is possible, and such immobilization improves the in vitro cell viability of PCL NFM; (2) immobilization of antibacterial nanoparticles (Ag) with PCL NFM is possible, and such immobilization improves the in vitro antibacterial activity of PCL NFM; (3) direct attachment of FN on a dental implant material (Ti-6Al-4V) is possible using tresyl chloride activation method; and (4) microgrooving of a Ti implant followed by coating the microgrooves with CG-PCL NFM significantly improves in vivo mechanical stability and osseointegration.

Figure 1:
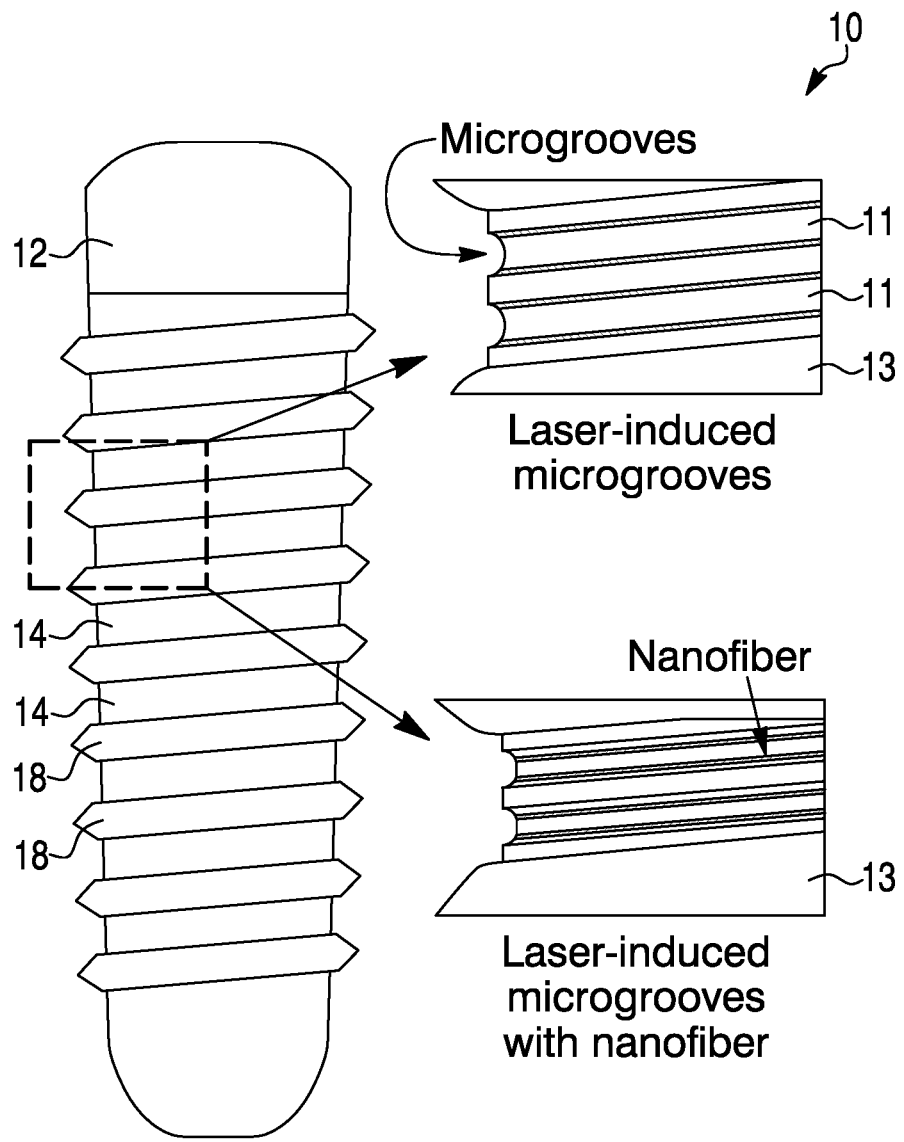
FIG. 1 is a non-limiting diagram showing microgrooves and nanofiber-assisted drug delivery on dental implant as provided by the present invention.

Referring to FIG. 1, in a preferred embodiment the present invention 10 provides coating methods described above to dental implants with the goal of improving the osseointegration of implants. We use a laser pulse to create microgrooves 11 at the interspace between two threads 18 of a dental implant (Di) 12. Laser-induced microgrooves 11 were shown in our research to significantly influence the surface morphology, contact angle, surface roughness, and chemical composition of Ti that can influence the attachment of fibronectin on implants. A set of continuous microgrooves 11 with 50 μm width, 5 μm depth, and 150 μm spacing between grooves are engraved at the root of the threads (~0.5 mm) on a Di 12 using a laser system (e.g., a Galvo FP fiber marking) to produce a laser-microgrooved Di 13. A rotary stage of the laser system (not shown) is oriented according to the helix angle of the implant threads to produce the laser microgrooves 11 at the root 14 of the threads 18.

As shown in FIG. 1, the microgrooves are parallel to each other and are oriented according to the helix angle of the thread, and the nanofiber is aligned with the helix angle of the microgrooves and thread.

Figure 2:
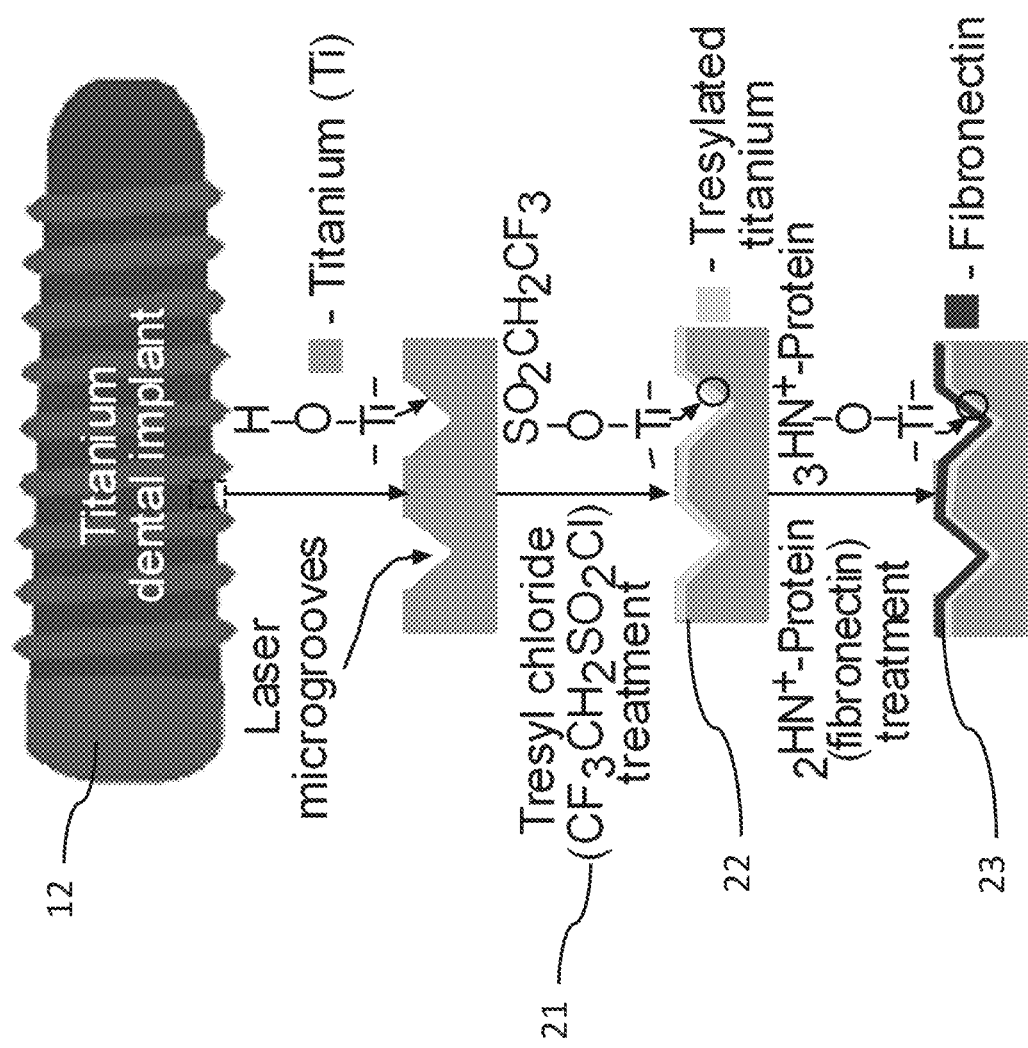
FIG. 2 is a non-limiting diagram showing the method of the present invention providing protein immobilization on Ti using nanofiber matrix as a functional coating.

Referring to FIG. 2, in a preferred embodiment FN is attach on the laser-engraved implant 12 surface by tresyl chloride method 21, and coats the FN-immobilized implant surface 22 with BMP2- and Ag-immobilized PCL NFM as shown 23. Basic terminal hydroxyl groups of a pure titanium surface 22 react with tresyl chloride, which allows for further coupling with fibronectin (FN). Previous in vivo studies using a rabbit femur model found that immobilizing fibronectin (FN) onto cylindrical pure titanium implants enhanced bone regeneration around implants. However, pure titanium has limited applications in the biomedical industry due to its inferior mechanical and biological properties, compared to biomedical grade titanium alloys, such as Ti-6Al-4V (the most commonly used titanium alloy in medical devices). We examined whether human plasma FN can be attached to Ti-6Al-4V via the tresyl chloride activation method. Three groups of samples were prepared to test the FN attachment on Ti via the tresyl chloride activation process: (1) control, (2) tresyl chloride-activated Ti (referred to as Tresyl/Ti), and (3) tresyl chloride-activated Ti subsequently coupled with FN (referred to as FN/Ti). To prepare Tresyl/Ti, the top surface of a polished Ti-6Al-4V sample was treated with 2,2,2-Trifluoroethanesulfonyl chloride at 36° C. for 48 hours, then washed with water, water-acetone (50:50), and acetone. Samples were then dried and stored in a desiccator. To prepare FN/Ti, a Tresyl/Ti sample was treated for 24 hours at 37° C. with human plasma fibronectin diluted in phosphate-buffered saline (PBS) solution to a concentration of 0.1 mg/mL. X-ray photoelectron spectroscopy (XPS) analysis was conducted on all samples to determine the chemical state of Ti. The binding energy for each spectrum was calibrated against the C1s peak at 284.8 eV.

Figure 3:
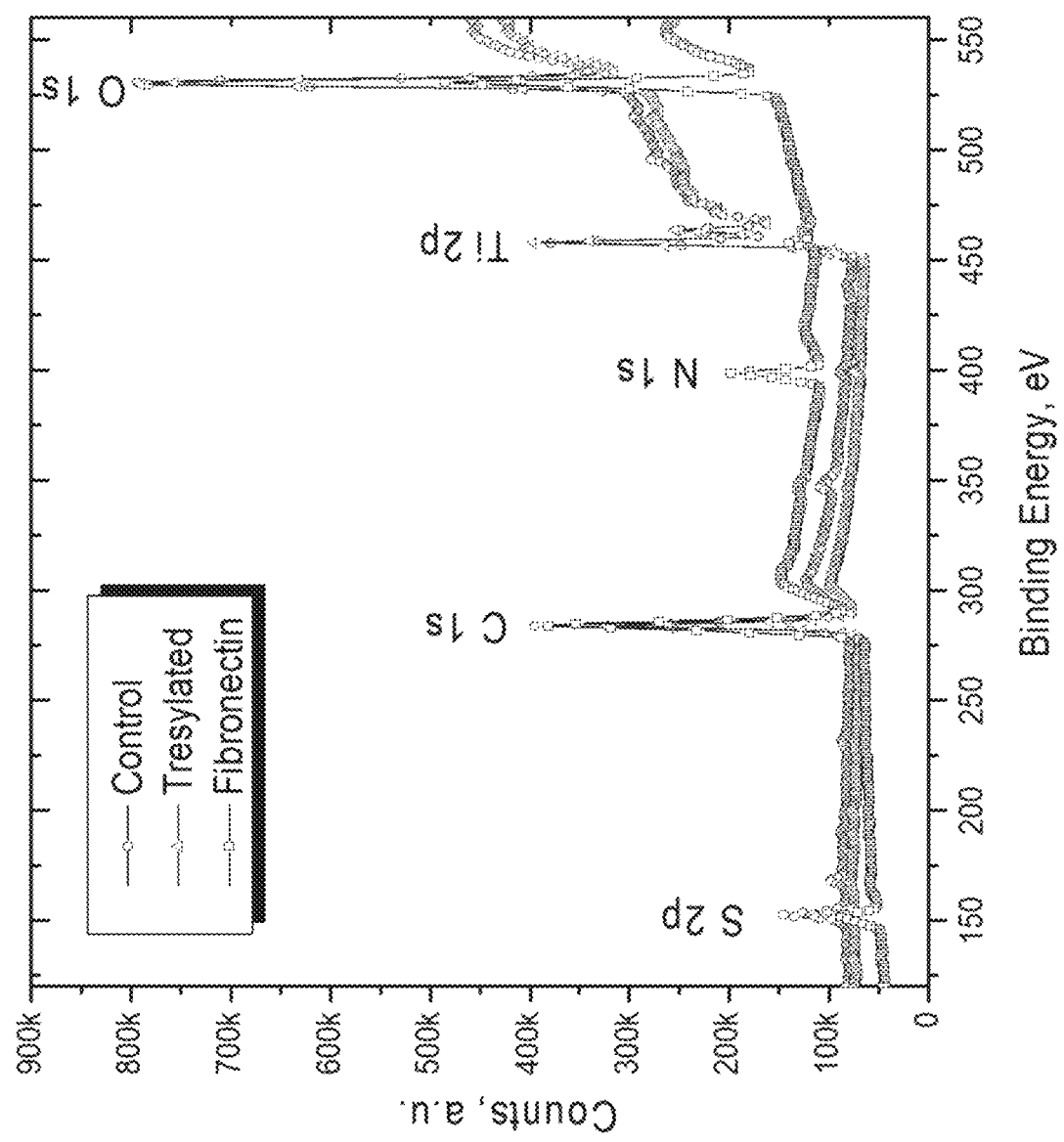
FIG. 3 is a non-limiting diagram showing F1s, S2p, N1s and O1s spectra of the Ti, Tresyl/Ti, and FN/Ti surface by a XPS analysis.

Referring to FIG. 3, XPS analysis found the presence of an amide group for FN/Ti, which confirms the surface activation by tresyl chloride and then direct coupling of FN with Ti. The N1s peak, derived from the amide bond of immobilized fibronectin, was detected around the binding energy of 400 eV for only FN/Ti samples. Therefore, this study suggested that direct attachment of FN is possible on a tresylated Ti alloy surface. Our proof of concept for the potential application of the treatment protocols on a Di led to the following: an ideal functional coating for a Di must reabsorb with time to allow and encourage new bone formation while maintaining its osteoconductive properties in vivo.

Figure 4:
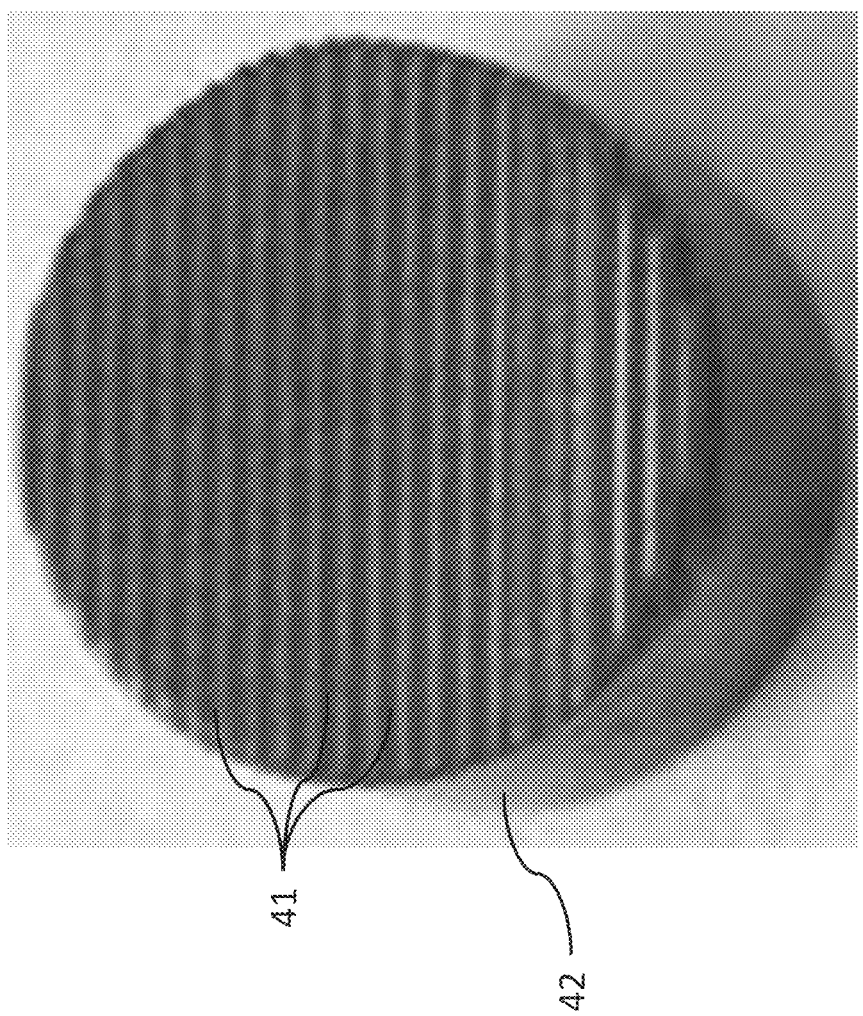
FIG. 4 is a non-limiting diagram showing precision microgrooves on the flat surface of a Ti rod fromed by the method of the present invention.

Referring to FIG. 4, the present invention provides laser engraving 41 to support attachment of FN on a dental implant (FIG. 1-12) and then coating the implant with BMP2 and Ag NP-immobilized PCL NFM. A laser pulse can be applied on the polished surfaces of Ti to create linear and continuous microgrooves on Ti implants. A laser capable of producing precision microgrooves (FIG. 1-11) on at least the flat surface of a Ti rod 42 can be used for this purpose. In our research we have used a Galvo FP fiber marking laser equipped with software for engraving a set of microgrooves (10 µm width, 5 µm depth, and 50 µm spacing between grooves) on Ti. The reason for achieving 5 µm-deep microgrooves on Ti is due to the fact that each groove of this size can accommodate at least 18 layers of nanofiber (average fiber diameter ~300 nanometers). In the present invention, we use 18 layers of PCL NFM because our research shows that the porosity of a PCL NFM membrane comprising 18 layers of fibers is adequate for cells to migrate through the membrane. FN can be attached on laser engraved Ti implants (lgTi), where immobilization of FN with Ti is accomplished by the tresyl chloride method as provided by the present invention.

Figure 5:
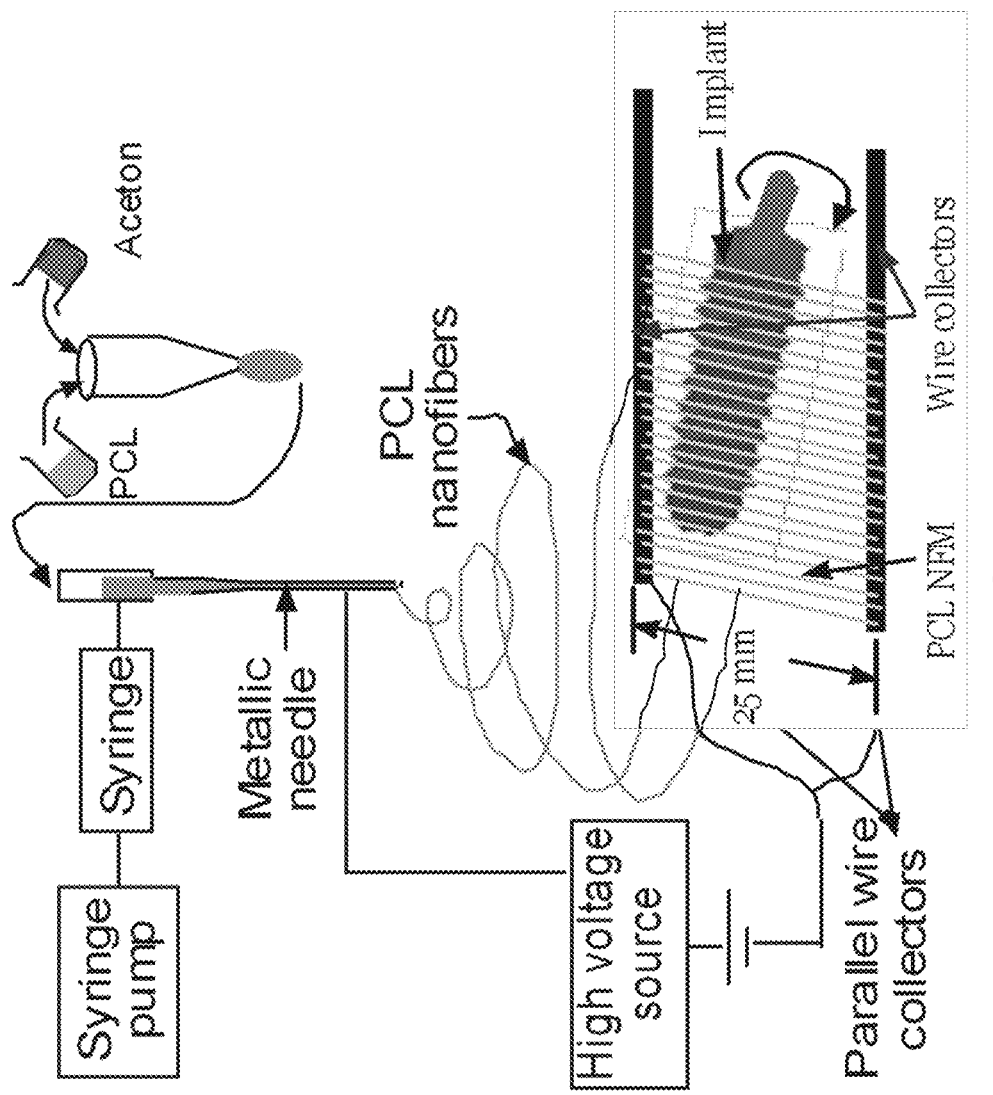
FIG. 5 is a non-limiting diagram showing schematic representation of the processes for preparing an in vivo dental implant.

Referring to FIG. 5, aligned unidirectional PCL NFM can be collected using the methods disclosed in U.S. Pat. No. 9,809,906 by the present Applicant and illustrated in FIG. 5. The laser-grooved surface of lgTi is activated by tresyl chloride and then 18 layers of PCL NFM is deposited along the direction of the thread (clockwise) by rotating the tresylated Di 18 times until the implant collects 18 layers of fibers. The reason for adapting this coating method on a Di surface is due to fact that such a method should be able to maintain nanofibers along the Di/bone interface. FN, FN-Hep-BMP2 and CG-Ag complexes are gently splashed on the PCL coated Di samples to prepare FN-PCL/Di, FN-BMP-PCL/Di and CG-Ag-PCL/Di Di, respectively. All implants are prepared under sterile conditions and kept for 30 minutes in a portable ultraviolet sterilizer before surgery.

Figure 6A:
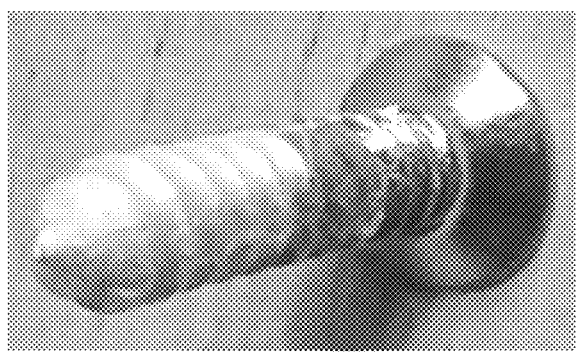
FIG. 6a is a non-limiting diagram showing a 3 mm diameter screw coated with 18 layers of PCL NFM.
Figure 6B:
FIG. 6b is a non-limiting diagram showing twisting of an NFM coated screw in to a pre-drilled hole (2.6 mm diameter) on a clear acrylic shows homogenous distribution of fiber along screw/acrylic interface.
Figure 7A:
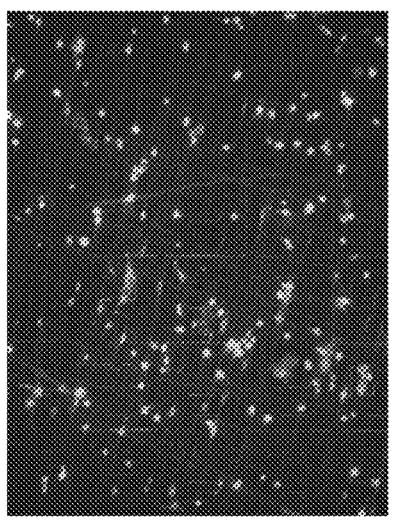
FIG. 7a is a non-limiting image showing individual immobilization of CG and FN on PCL NFM.
Figure 7B:
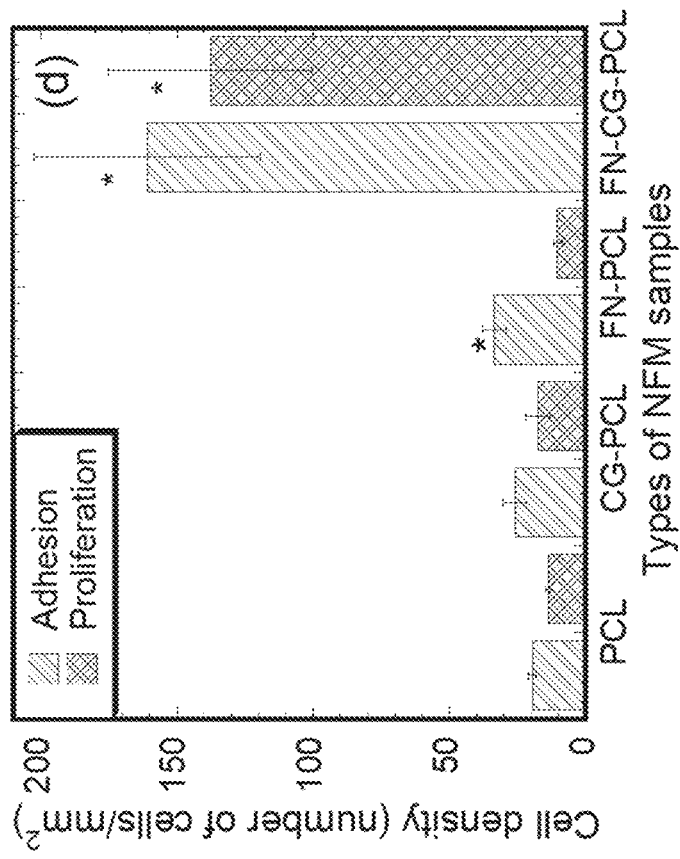
FIG. 7b is a non-limiting graph showing that the individual immobilization of CG and FN on PCL NFM has no adverse effect on osteoblast cells adhesion and proliferation of PCL NFM, and significant increase of cell adhesion observed for FN-PCL-NFM when compared to PCL NFM ($p<0.05$).

Referring to FIGS. 6a and 6b, in a method validation test we coated a M3×0.5 screw by PCL NFM using the method of the present invention (FIG. 5). We torqued the fiber-coated screw in to a pre-drilled hole (2.6 mm) on clear acrylic (FIG. 6b). We observed homogeneously-distributed fiber along the interface between the screw and the acrylic (FIG. 6b).

Experimental Aspects

Immobilization of Bone Morphogenic Protein-2 (BMP2) on Ti Using Fibronectin and PCL NFM.

Bone morphogenic proteins (BMPs) play important roles in in osteoblast and chondrocyte differentiation. Research shows that surface functionalization of Ti with BMP2 improves the osteoblast activities of Ti. Among BMP family members, BMP2 is a potent osteoinductive factor that plays key role during bone formation. Fibronectin (FN) is a multifunctional protein most abundantly found in the extracellular matrix (ECM) under dynamic remodeling conditions such as bone healing and development. Research shows that tethering of FN onto Ti effectively enhanced the bone regeneration around implants. Our preliminary studies show that FN-immobilized PCL NFM (referred as FN-PCL) has higher biocompatibility with osteoblast cells in comparison to PCL. FN contains binding domains for many bone growth signaling factors, including BMP2 and transforming growth factor-beta (TGF-β). We have successfully immobilized BMP2 with PCL NFM using FN in our preliminary studies. The effect of BMP2-immobilized PCL NFM coating on the osteogenic functions of Ti is not known and thus it needs to be investigated.

Immobilization of Silver Nanoparticles (Ag NP) on Ti Using Collagen and PCL NFM.

Prolonged anti-bacterial activities of an implant are possible by tethering anti-bacterial molecules with the implant. Many studies reported that Ag NP inhibits bacterial growth, while retaining/promoting osteoblast viability. Among common antibacterial nanoparticles (Ag, CuO, ZnO), Ag NP shows the minimum toxicity to environmentally relevant test organisms and mammalian cells in vitro and in vivo. Since Ag NP dissolves in CG, it can be immobilized with CG-PCL NFM. Our in vivo and in vitro studies show that CG-PCL NFM coating enhanced biological functions of Ti. This is due to the fact that higher cell functions were created via better cell signaling arising from the cell-cell contact and the cell-NFM components in the case of the CG-PCL NFM-coated Ti samples than non-coated Ti samples. Our preliminary studies showed no antimicrobial activity of Ag NP-immobilized CG-PCL NFM towards *Staphylococcus aureus* in comparison to PCL NFM. The effect of Ag NP-tethered CG-PCL NFM on the osteogenic and anti-bacterial activities towards other common aerobic bacterial organisms on Ti implant is not known and thus needs to be investigated.

Effect of Immobilization of Fibronectin and Collagen on the Cellular Functions of PCL NFM Fibronectin (FN) contains several active sites, known as the heparin-binding domains, collagen-binding domain, fibrin-binding domain, and cell-binding domain, that serve as platforms for cell anchorage. The goal of this preliminary study was to evaluate the effect of immobilization of collagen and plasma fibronectin with PCL NFM on the cellular functions of PCL NFM. The results (FIG. 7a and FIG. 7b) show that the individual immobilization of CG and FN on PCL NFM has no adverse effect on osteoblast cells adhesion and proliferation of PCL NFM, although a significant increase of cell adhesion was observed for FN-PCL-NFM when compared to PCL NFM ($p<0.05$). A significant improvement of cell adhesion and proliferation was observed for FN-CG-PCL NFM in comparison to PCL NFM ($p<0.01$). This is due to the fact that higher cell functions were created via better cell signaling arising from the cell-cell contact and the cell-NFM components in the case of FN-CG immobilized PCL NFM compared to PCL NFM.

Direct attachment of FN on a Ti implant surface is possible using a Tresyl Chloride-Activated Method (shown in Section C.5.). Since FN contains a CG binding domain, FN-immobilized Ti can therefore be polymerized into CG-PCL. The effect of the attachment of PCL NFM with Ti using CG and FN on the osteogenic functions of the implant is not known and needs to be investigated.

Immobilization of Human Bone Morphogenic Protein-2 (BMP2) with PCL NFM Using Fibronectin (FN).

Figure 8A:
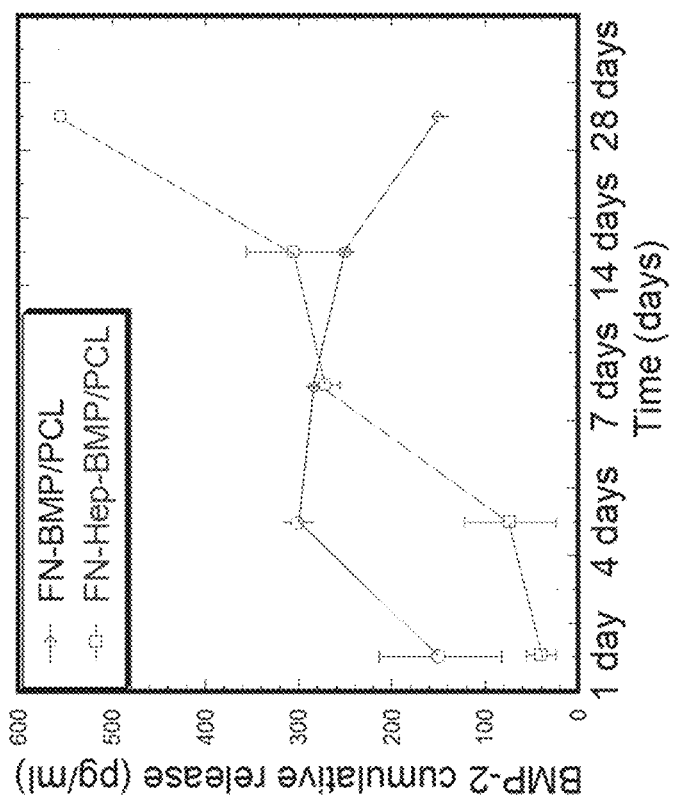
FIG. 8a is a non-limiting graph showing a gradual increase of release of BMP2 for 28 days was observed for FN-Hep-BMP2/PCL samples.
Figure 8B:
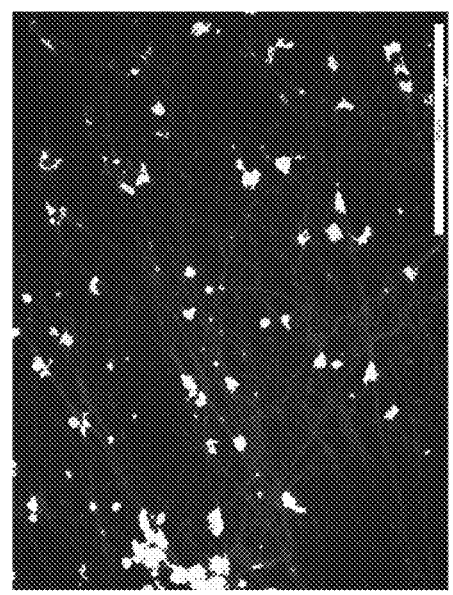
FIG. 8b is a non-limiting image showing cell divisions after 48 hours of cell culture on FN-BMP2-PCL samples.

The PCL NFM can be modified with heparin (Hep) and further immobilized with BMP2. The modified fibers showed the potential to effectively induce osteogenic differentiation of periodontal ligament cells. Since FN contains heparin-binding domains, PCL fibers can be modified with FN-Hep-BMP2 complex. The purpose of this preliminary study was threefold: (1) to immobilize BMP2 on PCL NFM using only FN-BMP2 and FN-Hep-BMP2 complexes, (2) to determine the amount of BMP2 release from the immobilized BMP2-PCL NFM, and (3) to compare the cell viability of BMP2-immobilized PCL NFMs with respect to PCL NFM (control). Immobilized BMP2 was released from the PCL NFMs in a sustained manner for 28 days, although the rates of release of BMP2 from FN-BMP2/PCL and FN-Hep-BMP2/PCL were different. A gradual increase of release of BMP2 for 28 days was observed for FN-Hep-BMP2/PCL samples (FIG. 8a). Rapid release of BMP2 for first 4 days, then gradual decline of release of BMP2 with time was observed for FN-BMP2/PCL samples. Cells displayed a well-extended morphology on all the BMP2-treated groups, when they were compared with the control group (8a). FIG. 8b depicts a representative image showing cell divisions after 48 hours of cell culture on FN-BMP2-PCL samples. In the image, blue color shows the attachment of cells on NFM. There was more than a 52% and 30% increase in the cell viability on FN-Hep-BMP2-PCL samples after culturing the cells for 72 hours compared to control and FN-BMP2-PCL. Both release and cell viability tests suggested an advantage of FN-Hep-BMP2 over FN-BMP2 complex for the immobilization of BMP2 with PCL NFM. FN-Hep-BMP2 immobilized PCL NFM has the potential to induce osteogenic differentiation of osteoblast cells on a Ti implant surface, which is not yet known. The effect of the treatment of Ti with FN by tresyl chloride method and then coating by FN-Hep-BMP2/PCL on the osteogenic functions needs to be investigated.

Attachment of Silver Nanoparticles (Ag NP) with PCL NFM Using CG

Figure 9B:
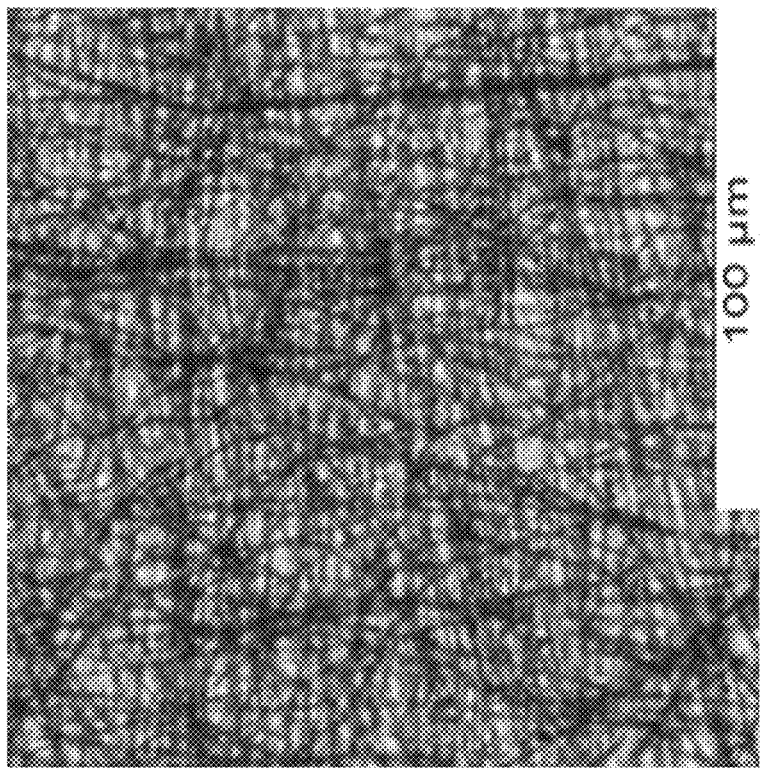
FIG. 9b is a non-limiting image showing CG-Ag-PCL samples after Gram staining.
Figure 9A:
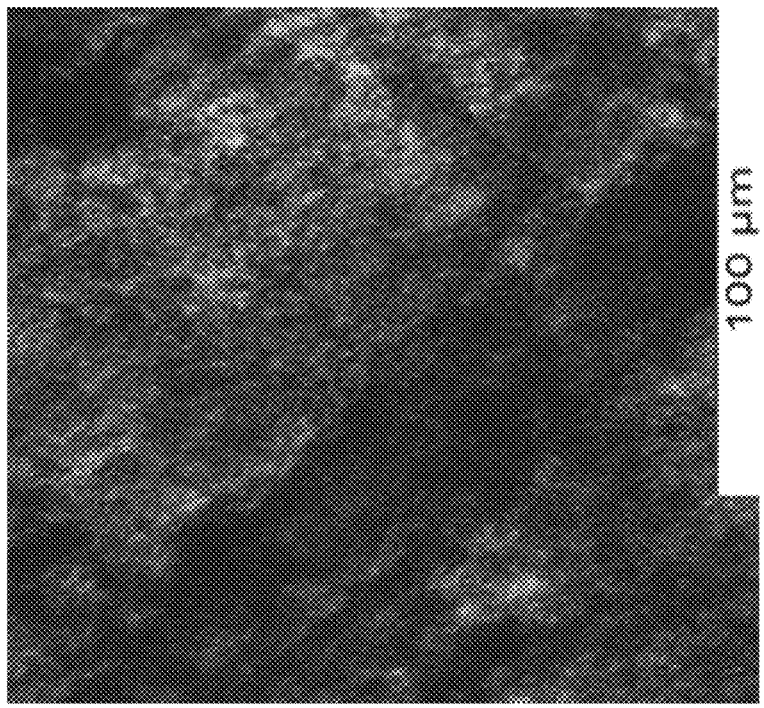
FIG. 9a is a non-limiting image showing PCL samples after Gram staining.
Figure 10:
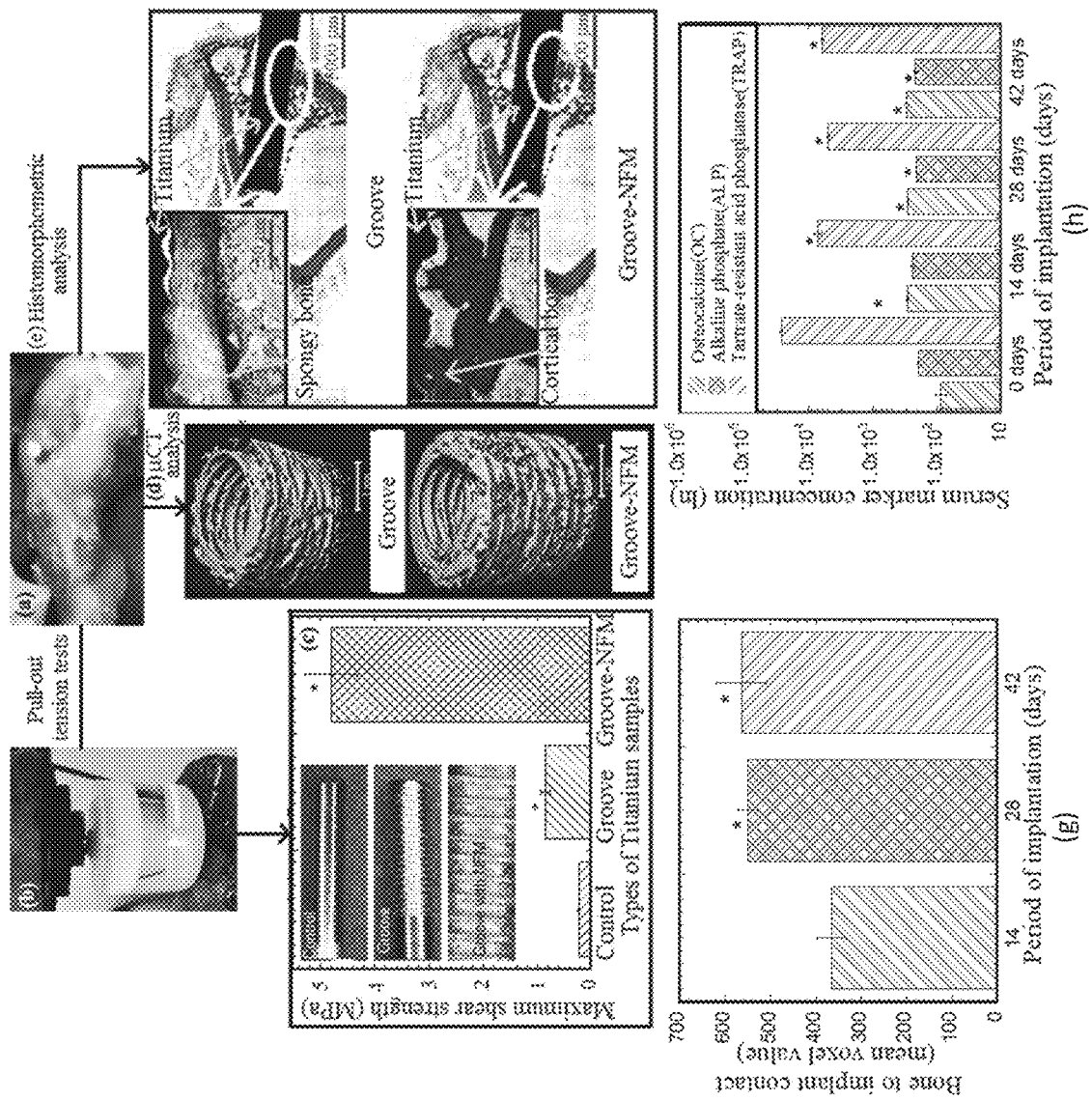
FIG. 10 is a non-limiting diagram presenting the test results of time-dependent bone growth around the CG-PCL NFM-coated Ti implant and related in vivo pull-out tests to demonstrate mechanical stability of microgrooved-Ti.

Silver nanoparticles (Ag NP) show promising anti-bacterial properties with biocompatibility and minimal toxicity. Ag NP-loaded collagen was immobilized with polymeric film to inhibit bacterial growth while promoting osteoblast cell viability. The anti-bacterial activities of PCL NFM can be improved by immobilizing Ag NP-loaded CG with PCL NFM. The purpose of this preliminary study was to examine the effect of immobilization of Ag NP-loaded CG on the anti-bacterial properties of PCL NFM. We succeeded in immobilizing Ag-loaded collagen with PCL NFM. The SEM and XRD analysis before and after 2 days of bacterial culture confirmed the presence of Ag with PCL. Our bacterial culture studies showed no sign of colonies growing on Ag-CG-PCL, whereas the presence of bacteria was observed in PCL. FIG. 9 shows PCL samples after Gram staining: (a) PCL and (b) CG-Ag-PCL. S. aureus that take up the Gram stain were present in PCL, as observed in the image by circular black shapes (pointed by arrows), while CG-Ag-PCL without S. aureus, did not stain and appears with a gray color. One reason for this might arise from an increased carrying capacity of Ag NP-loaded collagen by the nanofiber disc due to its unique surface-to-volume ratio.

In Vivo Evaluation of Coating a Titanium Implant with CG-PCL NFM

We have invented a method of coating a cylindrical metal implant with NFM that is made with CG-PCL (U.S. Pat. No. 9,809,906). Our invention implements a set of grooves that are created on Ti in a circumferential direction to increase the contact area between the implant and bone. CG-PCL NFM is subsequently coated along the sub-micrometer grooves on the Ti implant using our unique electrospinning process (U.S. Pat. No. 9,359,694). The goal of this research was to evaluate the effect of CG-PCL NFM coating on the mechanical stability and osseointegration of a Ti implant using a rabbit model. Our in vivo pull-out tests demonstrated that mechanical stability of microgrooved-Ti was significantly higher compared to non-grooved Ti. The mechanical stability (quantified by shear strength) of groove-NFM Ti/bone samples were significantly greater compared to other samples ($p<0.05$). The pull-out strength of groove-NFM-coated Ti was comparable to other functional coating-treated Ti reported in the literature. The types of new bone growth on Ti was different between groove and groove-NFM samples, which was observed from the stained images of histology-sectioned images (FIG. 10e). Histomorphometric results showed that the amount of BIC on Ti was higher for groove-NFM ($12.18\pm0.94$ mm, n=2) than groove ($5.30\pm4.01$ mm, n=2) samples. Due to the poor attachment of Ti with bone, Ti implants came out from their implant sites during histology preparation. Therefore, there was no result for any control sample. Both μCT analyses (FIG. 10e and FIG. 10f) and blood serum (FIG. 10g) results confirmed the time-dependent bone growth around the CG-PCL NFM-coated Ti implant and determined that 6 weeks were required for sufficient bone growth around the implant.

Our in vivo pull-out tests demonstrated that mechanical stability of microgrooved-Ti was significantly higher compared to non-grooved Ti (FIG. 10c). The mechanical stability (quantified by shear strength) of groove-NFM Ti/bone samples were significantly greater compared to other samples ($p<0.05$). The pull-out strength of groove-NFM-coated Ti was comparable to other functional coating-treated Ti reported in the literature. The types of new bone growth on Ti was different between groove and groove-NFM samples, which was observed from the stained images of histology-sectioned images (FIG. 10e). Histomorphometric results showed that the amount of BIC on Ti was higher for groove-NFM ($12.18\pm0.94$ mm, n=2) than groove ($5.30\pm4.01$ mm, n=2) samples. Due to the poor attachment of Ti with bone, Ti implants came out from their implant sites during histology preparation. Therefore, there was no result for any control sample. Both μCT analyses (FIG. 10e and FIG. 10f) and blood serum (FIG. 10g) results confirmed the time-dependent bone growth around the CG-PCL NFM-coated Ti implant and determined that 6 weeks were required for sufficient bone growth around the implant.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A method for improving osseointegration, functional load, and overall strength of intraosseous dental implants, the method comprising:
   providing a threaded endosseous dental device with a cylindrical shape and having an external thread extending from a root of the device along a helix angle with interspaces located between turns of the thread;
   creating laser-grooved surfaces consisting of two parallel microgrooves at the interspaces between the thread turns and oriented according to the helix angle of said thread to provide a helix angle of the microgrooves;
   activating said laser-grooved surfaces by applying tresyl chloride coupled with fibronectin (FN);

coating said laser-grooved surfaces with a nanofiber matrix (NFM) comprising at least one of growth factor or antibiotic-modified polycapronlectron (PCL) Electrospun Nanofibers (ENFs), said PCL-ENF combined with at least any of Platelet Derived Growth Factor (PDGF), Bone Morphogenetic Protein 2 (BMP2), PDGF+BMP2, or BMP2 and silver (Ag), and aligning said NFM with the helix angle of said microgrooves, wherein, said NFM adheres to said laser-grooved surfaces of said dental device.

2. The method of claim 1, wherein a rotary stage of a laser system is oriented according to the helix angle of said thread to engrave said microgrooves between said thread to create said laser-grooved surface.

3. The method according to claim 2, wherein said microgrooves are engraved to exhibit a capacity to hold 18 layers of nanofibers where microgroove depth is 5 µm.

4. The method according to claim 3, wherein said NFM comprises 18 fiber layers where said fibers are deposited along the helix angle of said microgrooves by circumferentially rotating said dental device until 18 layers of nanofibers are collected in said microgrooves and shielded from applied loads.

5. A method for improving osseointegration, functional load, and overall strength of intraosseous dental implants, the method comprising:
providing a threaded endosseous dental device with a cylindrical shape and having an external thread extending from a root of the device along a helix angle with interspaces located between turns of the thread;
creating laser-grooved surfaces consisting of two parallel microgrooves at the interspaces between the thread turns and oriented according to the helix angle of said thread to provide a helix angle of the microgrooves;
coating said laser-grooved surfaces with nanofiber (NF) comprising at least one of growth factor or antibiotic-modified biocompatible nanofiber, and aligning said NF with the helix angle of said microgrooves.

6. The method of claim 5, further comprising activating said laser-grooved surfaces to enhance NF adherence to said laser-grooved surfaces by applying tresyl chloride coupled with fibronectin (FN), wherein said NF adheres to said laser-grooved surfaces.

7. The method according to claim 6, wherein said microgrooves are engraved to exhibit a capacity to hold 18 layers of nanofibers where microgroove depth is 5 µm.

8. The method according to claim 7, wherein at least 18 layers of said NF is deposited to form layers along the helix angle of said microgrooves by circumferentially rotating said dental device until 18 layers of nanofibers are collected in said microgrooves and shielded from applied loads.

9. The method according to claim 8, wherein said microgrooves are engraved to a depth of 5 µm, a width of 50 µm, and a spacing of 50 µm to 150 µm between said grooves at the interspace of said thread.

10. The method of claim 9, wherein a rotary stage of a laser system is oriented according to the helix angle of said thread to engrave said microgrooves.

11. A method for improving osseointegration, functional load, and overall strength of intraosseous dental implants, the method comprising:
providing a threaded endosseous dental device with a cylindrical shape and having an external thread extending from a root of the device along a helix angle with interspaces located between turns of the thread;
creating laser-grooved surfaces consisting of two parallel microgrooves at the interspaces between the thread turns and oriented according to the helix angle of said thread to provide a helix angle of the microgrooves;
activating said laser-grooved surfaces by applying tresyl chloride coupled with fibronectin (FN);
coating said laser-grooved surfaces with nanofiber (NF) comprising at least one of growth factor or antibiotic-modified biocompatible nanofiber, and aligning said NF with the helix angle of said microgrooves,
wherein said biocompatible nanofiber comprises at least polycapronlectron (PCL) modified with heparin (Hep) and morphogenic protein-2 (BMP2).

12. The method of claim 11, further comprising attaching collagen loaded with silver nanoparticles (Ag NP) or antimicrobial analogs thereof to the dental device.

* * * * *

UNITED STATES PATENT AND TRADEMARK OFFICE
CERTIFICATE OF CORRECTION

| | |
|---|---|
| PATENT NO. | : 11,058,521 B2 |
| APPLICATION NO. | : 16/286005 |
| DATED | : July 13, 2021 |
| INVENTOR(S) | : Vagan Tapaltsyan et al. |

It is certified that error appears in the above-identified patent and that said Letters Patent is hereby corrected as shown below:

In the Specification

At Column 1, please delete Lines 26-29 and insert in its place the following:
-- This invention was made with government support under GM103447 awarded by the National Institutes of Health. The government has certain rights in the invention. --

Signed and Sealed this
Eighth Day of November, 2022

Katherine Kelly Vidal
*Director of the United States Patent and Trademark Office*